United States Patent [19]

Paul et al.

[11] 4,107,309

[45] Aug. 15, 1978

[54] SUBSTITUTED IMIDAZO[1,2-D]-AS-TRIAZINES

[75] Inventors: Rolf Paul, River Vale, N.J.; Judith Menschik, Tappan, N.Y.

[73] Assignee: American Cyanamid Company, Stamford, Conn.

[21] Appl. No.: 799,821

[22] Filed: May 23, 1977

[51] Int. Cl.[2] .................... A61K 31/53; C07D 471/04
[52] U.S. Cl. ...................................... 424/249; 544/184
[58] Field of Search .......................... 544/184; 424/249

[56] References Cited

U.S. PATENT DOCUMENTS 3,941,785   3/1976   Clarke et al. ................. 544/184

FOREIGN PATENT DOCUMENTS 1,440,722   6/1976   United Kingdom ................. 260/250

Primary Examiner—John M. Ford
Attorney, Agent, or Firm—Edward A. Conroy, Jr.

[57] ABSTRACT

This disclosure describes novel 5-substituted imidazo[1,2-d]-as-triazines useful as anti-asthmatic agents and as inhibitors of the enzyme cyclic-AMP phosphodiesterase.

6 Claims, No Drawings

SUBSTITUTED IMIDAZO[1,2-D]-AS-TRIAZINES

BRIEF SUMMARY OF THE INVENTION

This invention relates to new organic compounds and, more particularly, is concerned with novel 5-substituted imidazo[1,2-d]-as-triazines which may be represented by the following structural formula:

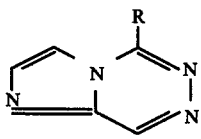

wherein R is methylthio, furfurylamino or 4-methyl-1-piperazinyl. The invention also includes novel compositions of matter containing the above-defined compounds and the method of meliorating psoriasis and/or asthma in mammals therewith.

DETAILED DESCRIPTION OF THE INVENTION

The novel compounds of the present invention possess anti-asthma activity at non-toxic doses and as such are useful as anti-asthmatic agents. Anti-asthma activity was determined by the mouse passive cutaneous anaphylaxis (PCA) test as follows.

Preparation of Mouse Immunoglobulins, IgE and IgG

Female mice (Charles River Breeding Labs.), weighing 20-22 gm. are inoculated intraperitoneally at approximately three weeks of age with 0.5 ml. of Timothy pollen antigen in complete Freund's adjuvant. The sensitizing antigen is prepared by suspending 60 mg. of Timothy antigen (Phleum pratense) in 6 ml. of Freund's Complete Adjuvant (Difco Labs.). Approximately 3-5 weeks after inoculation, ascitic fluid is removed from responding mice and tested for IgE and IgG type antibody by mouse PCA as follows:

Samples of ascitic fluid are diluted 1:10 and 50 μl are injected intradermally into five mice. The mice are challenged intravenously with antigen and Evans blue dye 48 hours later. Fifteen minutes after challenge, the dorsal skin is removed and examined for blue spots. Samples of ascitic fluid with IgE-type activity are pooled and titered to determine the dilution which gives a PCA lesion (area of blue) slightly greater than one centimeter in diameter. This dilution (typically 1:10) is then used routinely for that pool of fluid. To test for IgG activity, the ascitic fluid is diluted 1:40, 50 μl is injected intradermally and intravenous challenge is made 2 hours later. Samples of ascitic fluid with IgG type activity are pooled, heated at 56° C. for 4 hours and titered to obtain a PCA lesion slightly greater than one centimeter in diameter (Typically 1:40).

Passive Cutaneous Anaphylaxis Test

At −50 hour (relative to antigen challenge at 0 hour) 50 μl of IgE is injected intradermally on the left side of a 25 gm. female mouse, posterior to the axilla at the level of the diaphragm. At −2 hour, 50 μl of IgG is injected intradermally on the right side of the mouse. The mice are then place in individual cages and randomly assigned to control or treatment groups. Challenge and reading are performed in serial order so that reading of the assay is essentially blind. At −1 hour, the control animals received an intraperitoneal injection of 0.5 ml. of a 0.05% solution of carboxymethylcellulose in saline. For treatment animals, the test compound is dissolved or suspended in the carboxymethylcellulose-saline solution and administered intraperitoneally at −1 hour at 50 mg./kg. At 0 hour, the mice are anesthetized with ether and 0.5 ml. of saline containing 0.5 mg. of Timothy antigen and 2.5 mg. of Evans blue dye is injected into the tail vein. At +15 minutes the mice are sacrificed by cervical dislocation, the dorsal skin is removed and the blue PCA spots are examined on the inside surface. The largest and smallest diameters of the lesion and a qualitative estimate of intensity of color are recorded. The mean of the products of diameters (area) for mice in a given treatment group are compared with the control group. IgE and IgG lesions are analyzed independently. If the area for a treatment group is significantly smaller than the lesion area for the control group for either IgE or IgG lesion, the test compound is considered to be active as an anti-asthma agent. The results with a typical compound of this invention appear in Table I below.

TABLE I

| COMPOUND | MOUSE PCA TEST |
|---|---|
| 5-(4-methyl-1-piperazinyl)-imidazo[1,2-d]-as-triazine | Accept |

The novel compounds of the present invention are active in inhibiting the enzyme cyclic-AMP phosphodiesterase which is responsible for the metabolism of cyclic adenosine monophosphate which is usually simply referred to as cyclic AMP. As such, they are useful in the treatment of psoriasis, a disease in which the epidermal cyclic AMP levels are reported to be decreased. Also as such, they are useful in the treatment of asthma, since elevated levels of cyclic AMP in most cells are reported to inhibit the release of histamine and other mediators and since elevated levels of cyclic AMP in bronchial smooth muscle are reported to cause bronchodilation. See Ann. Reports in Medicinal Chem., Vol. 10, 197 (1975).

The inhibition of phosphodiesterase is determined by the mouse skin phosphodiesterase (PDE) inhibition test as follows:

Preparation of Mouse Skin PDE

Hairless mice (Jackson Laboratories), 3-4 months old are killed by cervical dislocation and their skins removed. Epidermal slices are taken at a thickness of 0.2 mm. The slices are weighed and homogenized at 100 mg./ml. in ice-cold tris-HCl buffer (0.04M, pH 8, containing 0.005M $MgCl_2$). Homogenates are centrifuged at 17,000 × gravity for 30 minutes. The supernatants are divided into aliquots which are stored at −20° C. Dilutions of the PDE are made with tris-HCl buffer just prior to use.

Anion Exchange Resin

AG1-X2 ®, 200-400 mesh (a polystyrene anionic exchange resin 8% cross linked from Bio-Rad Lab.) is washed with 0.5N HCl, 0.5N NaOH, 0.5N HCl and repeatedly with double distilled water to pH 5. The resin is allowed to settle and 2 volumes of water are added to one volume of settled resin.

Purification of $^3$H Cyclic AMP $^3$H-Cyclic AMP (21 c/m mole, Schwarz-Mann Inc.) is purified by addition of 0.1 to 0.2 ml. of stock (in 50% ethanol) to 5 ml. of anion exchange resin and 0.4 ml. of tris-HCl buffer. The mixture is vortexed, centrifuged at 1200 × gravity for 5 minutes and the supernatant is discarded. The resin is washed in the same manner eight more times with two volumes of tris-HCl buffer. Resin bound ³H-cyclic AMP is eluted by two successive washings with 4 ml. of 0.025N HCl (resin pH = 2.0). After centrifugation, the pooled acid washes containing ³H-cyclic AMP are aliquoted and lyophilized. The material is stored dry at −20° C. and reconstituted with tris-HCl buffer just prior to use with a volume sufficient to give approximately 200,000 CPM/0.1 ml.

PDE Assay

PDE activity is measured by the method of W. J. Thompson and N. N. Appleman, Biochemistry 10, 311 (1971). Assays are conducted in 12 × 75 mm. polypropylene test tubes. The reaction mixture consists of ³H-cyclic AMP (200,000 CPM), unlabeled cyclic AMP, PDE (100 ug. protein) and test compounds which are prepared by dissolving the compounds in methanol at a concentration of 10 mg./ml. and then dilution of tris-HCl buffer. Final concentration of the test compounds in the incubation mixture is 10 ug./ml. The total volume of the incubation mixture is increased to 0.4 ml. with tris-HCl buffer containing 3.75 millimoles of 2-mercaptoethanol. The enzyme is incubated for 10 minutes at room temperature in the presence of the test compounds or buffer prior to the addition of the mixture of ³H-cyclic AMP and unlabeled cyclic AMP. Reactions are run at 30° C. for 15 minutes and then terminated by immersing in acetone-dry ice until frozen, followed by boiling for 3 minutes. Tubes are cooled to room temperature. ³H-5′ AMP, formed in the reaction is converted to ³H-adenosine by the addition of 0.1 ml. of a solution of 5′-nucleotidase [16 ug./ml. in double distilled water Crotalus venom (Sigma Chemicals)] to the tubes which are incubated for 20 minutes at room temperature. This reaction is ended by the addition of one ml. of ice cold, stirred resin slurry which binds charged nucleotides (including ³H-cyclic AMP) but not ³H-adenosine. Tubes are vortexed and immersed in an ice bath for 15 minutes and then centrifuged at 1200 × gravity for 5 minutes. A 0.5 ml. portion is taken from each, placed in liquid scintillation vials with 10 ml. of Ready-Solv VI (Beckman Ind.) and counted for radio activity. Assay "blanks", determined with assay buffer substituted for PDE are less than 1% of total ³H-cyclic AMP added when ³H-cyclic AMP is purified as indicated.

Criterion for Activity as Inhibitor of Skin
(A) or Lung (B) Phosphodiesterase A compound is considered active if it inhibits more than theophylline, that is, to 50% of control at 1 mM concentration of compound, or to 80% of control of 0.05 mM concentration of compound. The results with the novel compounds of the present invention on inhibition of phosphodiesterase are recorded in Table II below.

TABLE II

| Compound | Mouse Skin Phosphodiesterase |
|---|---|
| 5-(Methylthio)-imidazo[1,2-d]-as-triazine | Active |
| 5-(4-Methyl-1-piperazinyl)-imidazo[1,2-d]-as-triazine | Active |
| 5-(Furfurylamino)- | |

TABLE II-continued

| Compound | Mouse Skin Phosphodiesterase |
|---|---|
| -imidazo[1,2-d]-as-triazine | Active |

The novel compounds of the present invention have thus been found to be highly useful for meliorating asthma and for inhibiting the enzyme phosphodiesterase in mammals when administered in amounts ranging from about 1.0 millgram to about 100.0 mg. per kilogram of body weight per day. A preferred dosage regimen for optimum results would be from about 5.0 mg. to about 50.0 mg. per kilogram of body weight per day, and such dosage units are employed that a total of from about 0.35 gram to about 3.5 gram of active compound for a subject of about 70 kg. of body weight are administered in a 24 hour period. The dosage regimen may be adjusted to provide the optimum therapeutic response. For example, several divided doses may be administered daily or the dose may be proportionally reduced as indicated by the exigencies of the therapeutic situation. A decided practical advantage of this invention is that the active compounds may be administered in any convenient manner such as by the oral, intravenous, intramuscular, or subcutaneous routes, and also by inhalation therapy including aerosol sprays.

Compositions according to the present invention having the desired clarity, stability and adaptability for parenteral use are obtained by dissolving from 0.10% to 10.0 % by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl -α-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg./ml. of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 250 and 500 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The invention will be described in greater detail in conjunction with the following specific examples.

EXAMPLE 1

Imidazo[1,2-d]-as-triazine-5(6H)-thione

N-Benzylimidazole is converted to 2-hydroxymethylimidazole by the method of R. G. Jones, J.A.C.S. 71, 383 (1949). The 2-hydroxymethylimidazole is converted to imidazole-2-carboxaldehyde by the method of H. Schubert and H. D. Rudorf, Angew. Chem. Intern. Ed., 5, 674 (1966). A 67.) gm. portion of imidazole-2-carboxaldehyde is added to 500 ml. of ethanol and warmed on a steam bath. An 85.4 gm. portion of methyl dithiocarbazate is added together with 200 ml. of ethanol. While the solution is warm, 20 drops of glacial acetic acid are added. The mixture is heated to reflux on a steam bath for one hour, cooled and filtered. The filtrate is evaporated yielding 123.2 gm. of 3-(2-imidazolymethylene)-dithio-carbazic acid, methyl ester. A 120.2 g. portion of 3-(2-imidazolylmethylene)dithiocarbazic acid, methyl ester is added to 800 ml. of diphenyl ester. The mixture is heated in an oil bath at 195°–200° C. for 15 minutes. The reaction mixture is cooled to room temperature and the precipitate is collected, washed with petroleum ether, and air dried. This light orange solid is crystallized twice from petroleum ether giving 83.0 gm. of imidazo[1,2-d]-as-triazine-5(6H)-thione, m.p. 238°–240° C.

EXAMPLE 2

5-(Methylthio)-imidazo[1,2-d]-as-triazine

A 66.7 gm. portion of imidazo[1,2-d]-as-triazine-5(6H)-thione is added to 250 ml. of ethanol. A solution of 10.1 gm. of sodium reacted in 250 ml. of ethanol is added with swirling. A 27.7 ml. portion of methyl iodide is added slowly with swirling. The mixture is stored in a chillroom overnight, filtered and dried giving 56.5 gm. of the desired final product, m.p. 147°–149° C.

EXAMPLE 3

5-(4-Methyl-1-piperazinyl)-imidazo[1,2-d]-as-triazine

A 5.0 gm. portion of 5-(methylthio)-imidazo[1,2-d]-as-triazine is combined with 45 ml. of N-methylpiperazine and refluxed for 5 hours. The reaction mixture is evaporated giving a brown oil. This oil is triturated four times with 30 ml. portions of hot benzene. The combined benzene solutions are treated with charcoal, evaporated to 75 ml., retreated with charcoal, cooled and filtered, giving 1.0 gm. of the desired product, m.p. 176°–178° C. This base forms non-toxic acid-addition salts with a variety of pharmacologically acceptable organic and inorganic salt-forming reagents. Thus, acid-addition salts, formed by admixture of the organic free base with an equivalent of an acid, suitably in a neutral solvent, are formed with such acids as sulfuric, phosphoric hydrochloric, sulfamic, citric, lactic, tartaric, acetic, benzoic, gluconic, ascorbic, and related acids. For purposes of this invention, 5-(4-methyl-1-piperazinyl)-imidazo[1,2-d]-as-triazine is equivalent to its non-toxic acid-addition salts.

EXAMPLE 4

5-(Furfurylamino)-imidazo[1,2-d]-as-triazine

A 5.0 gm. portion of 5-(methylthio)-imidazo[1,2-d]-as-triazine is combined with 45 ml. of furfurylamine and refluxed for 2 hours. The mixture is allowed to stand at room temperature overnight. The gummy solid is collected and crystallized from 60 ml. of hot methanol, giving 2.75 gm. of the desired product as crystals, m.p. 212°–214° C.

EXAMPLE 5

| Preparation of 50 mg. Tablets | | |
|---|---|---|
| Per Tablet | | Per 10,000 Tablets |
| 0.050 gm. | 5-(methylthio)-imidazo-[1,2-d]-as-triazine | 500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | Magnesium Stearate (1%) | 15 gm. |
| 0.150 gm. | | 1490 gm. |

The 5-(methylthio)-imidazo[1,2-d]-as-triazine, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 6

| Preparation of Oral Suspension | |
|---|---|
| Ingredient | Amount |
| 5-(4-methyl-1-piperazinyl)-imidazo[1,2-d]-as-triazine | 500 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |
| Distilled water qs to | 100 ml. |

The sorbitol solution is added to 40 ml. of distilled water and the 5-(4-methyl-1-piperazinyl)-imidazo[1,2-d]-as-thiazine is suspended therein. The saccharin, sodium benzoate, flabor and dye are added and dissolved. The volume is adjusted to 100 ml. with distilled water. Each ml. of syrup contains 5 mg. of 5-(4-methyl-1-piperazinyl)-imidazo[1,2-d]-as-triazine.

EXAMPLE 7

Preparation of Parenteral Solution

In a solution of 700 ml. of propylene glycol and 200 ml. of water for injection is suspended 20.0 grams of 5-(furfurylamino)-imidazo[1,2-d]-as-triazine with stirring. After suspension is complete, the pH is adjusted to 5.5 with hydrochloric acid and the volume is made up to 1000 ml. with water for injection. The formulation is sterilized, filled into 5.0 ml. ampoules each containing 2.0 ml. (representing 40 mg. of drug) and sealed under nitrogen.

EXAMPLE 8

| Preparation of Aerosol Spray | |
|---|---|
| A suspension is prepared of: | |
| 5-(methylthio)-imidazo[1,2-d]-as-triazine; micronized (0.5–5.0 microns) | 400 mg. |
| Dichlorodifluoromethane | 100 ml. |
| Sorbitan trioleate | 6.0 mg. |

The active ingredient and sorbitan trioleate are placed in a beaker and the dichlorodifluoromethane is added at −40° C. whereupon a suspension is formed. The mixture is sonified, that is, treated with a Sonifier, manufactured by the Branson Sonic Power Co. of Danbury, Conn., as model LS-75 at a current input of 9 amperes for 2 minutes. Additional cold dichlorodifluoromethane is added as necessary to keep the volume at 100 ml. The mixture is uniformly dispersed, and has increased stability resulting from the sonification. Each of six 19 ml. stainless steel containers are filled with 15 ml. of the cold mixture, then valves are inserted and sealed in place. On warming, after storage, the 5-(methylthio)-imidazo[1,2-d]-as-triazine remains dispersed and, after merely casual shaking gives uniform doses of finely divided drug.

We claim:

1. 5-(Methylthio)-imidazo[1,2-d]-as-triazine.

2. A compound selected from the group consisting of 5-(4-methyl-1-piperazinyl)-imidazo-[1,2-d]-as-triazine and the non-toxic acid-addition salts thereof.

3. 5-(Furfurylamino)-imidazo[1,2-d]-as-triazine.

4. The method of meliorating asthma in a mammal which comprises administering internally to said mammal an effective amount of a compound selected from the group consisting of 5-(methylthio)-imidazo[1,2-d]-as-triazine, 5-(4-methyl-1-piperazinyl)-imidazo[1,2-d]-as-triazine and 5-(furfurylamino)-imidazo[1,2-d]-as-triazine.

5. A therapeutic composition in dosage unit form useful for meliorating asthma in mammals comprising from about one milligram to about one hundred milligrams per kilogram of body weight per daily dosage unit, in association with a pharmaceutical carrier, of a compound selected from the group consisting of 5-(methylthio)-imidazo[1,2-d]-as-triazine, 5-(4-methyl-1-piperazinyl)-imidazo[1,2-d]-as-triazine and 5-(furfurylamino)-imidazo[1,2-d]-as-triazine.

6. The process of preparing 5-(methylthio)-imidazo[1,2-d]-as-triazine which comprises treating imidazo[1,2-d]-as-triazine-5(6H)-thione with sodium ethoxide and methyl iodide in ethanol as solvent at ambient temperatures for a period of time of from about 10 to about 15 hours.

* * * * *